US009232981B2

(12) United States Patent
Kuo et al.

(10) Patent No.: US 9,232,981 B2
(45) Date of Patent: Jan. 12, 2016

(54) SURGICAL HOLDER

(71) Applicant: National Taiwan University of Science and Technology, Taipei (TW)

(72) Inventors: Chin-Hsing Kuo, Taipei (TW); Shao-Jung Lai, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 0 days.

(21) Appl. No.: 14/335,318

(22) Filed: Jul. 18, 2014

(65) Prior Publication Data

US 2015/0136926 A1 May 21, 2015

(30) Foreign Application Priority Data

Nov. 19, 2013 (TW) .............................. 102142006 A

(51) Int. Cl.
| F16M 13/02 | (2006.01) |
| A61B 19/00 | (2006.01) |
| F16M 11/12 | (2006.01) |
| A61B 1/00 | (2006.01) |
| A61B 19/02 | (2006.01) |

(52) U.S. Cl.
CPC .............. *A61B 19/26* (2013.01); *A61B 1/00149* (2013.01); *F16M 11/12* (2013.01); *F16M 13/022* (2013.01); *A61B 19/0256* (2013.01); *A61B 2019/263* (2013.01); *A61B 2019/265* (2013.01)

(58) Field of Classification Search
CPC .............. A61B 19/0256; A61B 19/26; A61B 2019/265; A61B 2019/263; A61B 2019/0259; F16M 13/022
See application file for complete search history.

(56) References Cited

U.S. PATENT DOCUMENTS 5,279,309 A * 1/1994 Taylor ................ A61B 19/5244
600/595
5,397,323 A * 3/1995 Taylor ................ A61B 19/2203
606/130

(Continued)

FOREIGN PATENT DOCUMENTS

DE 4334069 A1 * 4/1995 ............. A61B 19/26
DE 102013004459 A1 * 6/2014 ........... A61B 19/201

(Continued)

OTHER PUBLICATIONS

Lai et al., "Design of a Novel Passive Statically Balancing Laparoscope Holder", National Taiwan Univeristy of Science and Technology (published Jul. 24, 2013).

(Continued)

*Primary Examiner* — Terrell McKinnon
*Assistant Examiner* — Eret McNichols
(74) *Attorney, Agent, or Firm* — Mintz Levin Cohn Ferris Glovsky and Popeo, P.C.; Peter F. Corless; Steven M. Jensen

(57) ABSTRACT

A surgical holder is provided, including a base unit, a first positioning unit, a second positioning unit, a connecting unit, a first orientating unit, and a second orientating unit. The first elastic element, the second elastic element, the plurality of third elastic elements and the plurality of the fourth elastic elements balance the surgical holder statically. Further, the connecting unit, the first and second orientating units are designed to have RCM points which restrict lateral displacement of the surgical holder on the surgical incision to increase safety in laparoscopic operations.

10 Claims, 5 Drawing Sheets

(56) References Cited

U.S. PATENT DOCUMENTS

| | | | | |
|---|---|---|---|---|
| 6,246,200 B1* | 6/2001 | Blumenkranz | A61B 19/22 | 128/DIG. 7 |
| 6,424,885 B1* | 7/2002 | Niemeyer | A61B 19/22 | 600/109 |
| 6,676,669 B2* | 1/2004 | Charles | A61B 19/22 | 606/1 |
| 7,892,243 B2* | 2/2011 | Stuart | A61B 19/22 | 606/130 |
| 8,910,913 B2* | 12/2014 | Hirose | A61B 1/00149 | 248/123.11 |
| 8,911,429 B2* | 12/2014 | Olds | B25J 9/10 | 340/12.22 |
| 2003/0109780 A1* | 6/2003 | Coste-Maniere | A61B 19/22 | 600/407 |
| 2004/0024385 A1* | 2/2004 | Stuart | A61B 19/22 | 606/1 |
| 2004/0246469 A1* | 12/2004 | Hirose | A61B 1/00048 | 356/139.03 |
| 2005/0043718 A1* | 2/2005 | Madhani | A61B 19/22 | 606/1 |
| 2005/0161176 A1* | 7/2005 | Brenner | A61B 19/081 | 160/348 |
| 2006/0074406 A1* | 4/2006 | Cooper | A61B 19/2203 | 606/1 |
| 2006/0167440 A1* | 7/2006 | Cooper | A61B 19/2203 | 606/1 |
| 2006/0225529 A1* | 10/2006 | Fischer | A61B 19/26 | 74/469 |
| 2007/0080275 A1* | 4/2007 | Stachowski | A61B 8/00 | 248/323 |
| 2007/0173976 A1* | 7/2007 | Schena | A61B 19/22 | 700/245 |
| 2008/0167750 A1* | 7/2008 | Stahler | A61B 17/12172 | 700/245 |
| 2011/0071473 A1* | 3/2011 | Rogers | A61B 1/00149 | 604/167.01 |
| 2011/0071543 A1* | 3/2011 | Prisco | A61B 17/0218 | 606/130 |
| 2012/0080041 A1* | 4/2012 | Skora | A61B 19/081 | 128/851 |
| 2012/0158014 A1* | 6/2012 | Stefanchik | A61B 19/22 | 606/130 |
| 2012/0182134 A1* | 7/2012 | Doyle | A61B 1/00149 | 340/12.22 |
| 2015/0018622 A1* | 1/2015 | Tesar | A61B 1/05 | 600/202 |

FOREIGN PATENT DOCUMENTS

| | | | | |
|---|---|---|---|---|
| JP | WO 2005084573 A1 * | 9/2005 | | A61B 19/52 |
| JP | WO 2013018908 A1 * | 2/2013 | | B25J 13/02 |

OTHER PUBLICATIONS

Lai et al., "Design of a Novel Passive Statically Balancing Laparoscope Holder" (published Jul. 30, 2013).

Lai et al., "Design of a Novel Passive Statically Balancing Laparoscope Holder", 16th CSMMT (published Nov. 1, 2013).

* cited by examiner

SURGICAL HOLDER

CROSS-REFERENCES TO RELATED APPLICATIONS

This application claims under 35 U.S.C. §119(a) the benefit of Taiwanese Application No. 102142006, filed Nov. 19, 2013, the entire contents of which is incorporated herein by reference.

BACKGROUND OF THE INVENTION

1. Field of the Invention

The present invention relates to surgical holders, and, more particularly, to a novel surgical holder applicable to laparoscopic operations.

2. Description of Related Art

Due to the evolution of medical techniques in non-invasive and minimally invasive surgical procedures, various surgical assisting devices that are required for performing laparoscopic operations emerge vigorously. In laparoscopic operations, usually the surgeon would require an assistant to physically hold the laparoscope in order to adjust the required positions, orientations and angles to smoothly perform the surgery. Therefore, specific surgical holders for use on laparoscopic operations have been employed to replace the need for an assistant to hold the laparoscope during surgery, which not only reduces the necessity of manual power but also potential risks involved in inappropriate manipulations of the device/equipment during surgical procedures.

The surgical holders currently available on the market are classified into an initiative type and a passive type. The initiative-type holder is equipped with a motor for the control of positions, orientations and angles of the laparoscope. While the motor-assisted holder provides convenience in manipulating a laparoscope, it is not only costly to implement but also the overall structure is cumbersome to operate. The passive-type holder is to be operated manually by the surgeon, and is structurally compact and low-cost while providing relatively instinctive manipulations as compared to motor-assisted surgical holders. However, all currently available passive-type surgical holders on the market require a mechanical latch connector to perform lock-in and release motions in order to achieve good control of positions, orientations and angles of the laparoscope as required. In particular, during surgery the surgeon first needs to adjust a passive-type surgical holder to the required position, orientation and angle, and then also requires the step of lock-in motion, or unlocking the latch connector if any further adjustment of positions, orientations and angles are required during the procedures. Naturally such an operational step would bring great inconvenience to the surgeon in use of the equipment.

Moreover, most of conventional laparoscopic holders are designed to use the body of a patient as a supporting point in order to manipulate the laparoscope freely. However, using a surgical incision as a supporting point especially in large-scale rotation is liable to increase the lateral force on the patient's abdominal incision which is likely to cause injury or expand the abdominal incision as a result.

Therefore, it is highly desirable to propose a novel surgical holder which does not require a mechanical latch connector or any drive motor for latching or unlatching motions in order to position the laparoscopic holder on the required position, orientation and angle, and also can restrict the lateral displacement of the abdominal incision and facilitate the surgery, thus simplifying operational procedures while also eliminating the burden of having a conventional laparoscope placed upon a patient which is likely to cause injury or expand the abdominal incision due to the expanded lateral force.

SUMMARY OF THE INVENTION

In view of the drawbacks associated with the prior techniques, the present invention proposes a surgical holder which employs a statically balanced mechanism design and thus does not require a mechanical latch connector or any drive motor for latching or unlatching motions in order to position the laparoscopic holder on the required position, orientation and angle. In addition, the surgical holder is able to restrict the lateral displacement of the abdominal incision to facilitate the surgery, simplify the operational procedures while eliminating the burden of having a conventional laparoscope placed upon a patient, provide greater convenience in use, and also can be implemented at a low cost.

To achieve the above and other objectives, the present invention proposes a surgical holder, comprising: a base unit having a primary link; a first positioning unit having one end thereof pivotally connected to the primary link and having a first elastic element built therein; a second positioning unit having one end thereof pivotally connected to the other end of the first positioning unit and having a second elastic element built therein; a connecting unit having one end thereof pivotally connected to the other end of the second positioning unit and the other end including a first component having a first shaft hole and a second component having a second shaft hole, wherein an angle is included between the first component and the second component such that a shaft direction of the first shaft hole and a shaft direction of the second shaft hole intersect at a same point; a first orientating unit including a first orientation link, a first parallel connecting link set, a third pseudo base and a first supporting link, wherein the first orientation link has a first shaft rod pivotally connected to the first shaft hole, one end of the first parallel connecting link set is pivotally connected to the first orientation link, the other end of the first parallel connecting link set is pivotally connected to the third pseudo base and the first supporting link, and the first orientating unit has a plurality of third elastic elements built therein; and a second orientating unit including a second orientation link, a second parallel connecting link set, a fourth pseudo base and a second supporting link, wherein the second orientation link has a second shaft rod pivotally connected to the second shaft hole, one end of the second parallel connecting link set is pivotally connected to the second orientation link the other end of the second parallel connecting link set is pivotally connected to the fourth pseudo base and the second supporting link, and the second orientating unit has a plurality of fourth elastic elements built therein; wherein the first elastic element, the second elastic element, the plurality of third elastic elements and the plurality of the fourth elastic elements balance the surgical holder statically.

In an embodiment, the first positioning unit further comprises a first connecting link, a first auxiliary link and at least a first pseudo base, one end of the first connecting link and one end of the first auxiliary link are pivotally connected to the primary link, two ends of the first pseudo base are pivotally connected to the first connecting link and the first auxiliary link, respectively, the first connecting link is parallel to the first auxiliary link, the first pseudo base is parallel to the primary link, and a shaft direction of the primary link is parallel to a gravity direction.

In an embodiment, two ends of the first elastic element are connected to a mass center position of the first pseudo base and a mass center position of the first auxiliary link, respectively.

In an embodiment, the second positioning unit further includes a second connecting link, a second auxiliary link and at least a second pseudo base, one end of the second connecting link is pivotally connected to the other end of the first connecting link, one end of the second auxiliary link is pivotally connected to the other end of the first connecting link, two ends of the second pseudo base are pivotally connected to the second connecting link and the second auxiliary link, respectively, the second connecting link is parallel to the second auxiliary link, and the second pseudo base is parallel to the primary link.

In an embodiment, two ends of the second elastic element are connected to a mass center position of the second pseudo base and a mass center position of the second auxiliary link, respectively.

In an embodiment, the surgical holder further comprises a plurality of connectors for pivotally connecting with the primary link, the first connecting link, the first auxiliary link, the first pseudo base, the second connecting link, the second auxiliary link, the second pseudo base and the connecting unit, wherein the connectors are axially parallel to each other.

In an embodiment, the first parallel connecting link set includes a plurality of first pivot connectors each having its shaft direction parallel to each other, the second parallel connecting link set includes a plurality of second pivot connectors each having its shaft direction parallel to each other, a first holding link is disposed at one end of the first supporting link that is not pivotally connected to the first parallel connecting link set, a shaft direction of the first holding link is parallel to a shaft direction of the first pivot connectors, a second holding link is disposed at one end of the second supporting link that is not pivotally connected to the second horizontal connecting link, and a shaft direction of the second holding link is parallel to a shaft direction of the second pivot connectors.

In an embodiment, the surgical holder further comprises a sheath having a sliding groove formed on a surface thereof, wherein the first holding link and the second holding link abut against the sliding groove to slide within the sliding groove, shaft directions of the sheath, the first shaft hole and the second shaft hole intersect at one point.

In an embodiment, the first elastic element, the second elastic element, the third elastic elements and the fourth elastic elements are springs.

In an embodiment, each of the third elastic elements is disposed between the first parallel connecting link set and a vertical portion of the first orientation link and between the third pseudo base and the first supporting link, each of the fourth elastic elements is disposed between the second parallel connecting link set and a vertical portion of the second orientation link and between the fourth pseudo base and the second supporting link, the third pseudo base is parallel to the vertical portion of the first orientation link, and the fourth pseudo base is parallel to the vertical portion of the second orientation link.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE PREFERRED EMBODIMENTS

The following illustrative embodiments are provided to illustrate the disclosure of the present invention, these and other advantages and effects can be understood by persons skilled in the art after reading the disclosure of this specification. Note that the structures, proportions, sizes depicted in the accompanying figures merely serve to illustrate the disclosure of the specification to allow for comprehensive reading without a limitation to the implementation or applications of the present invention, and does not constitute any substantial technical meaning.

Figure 1:
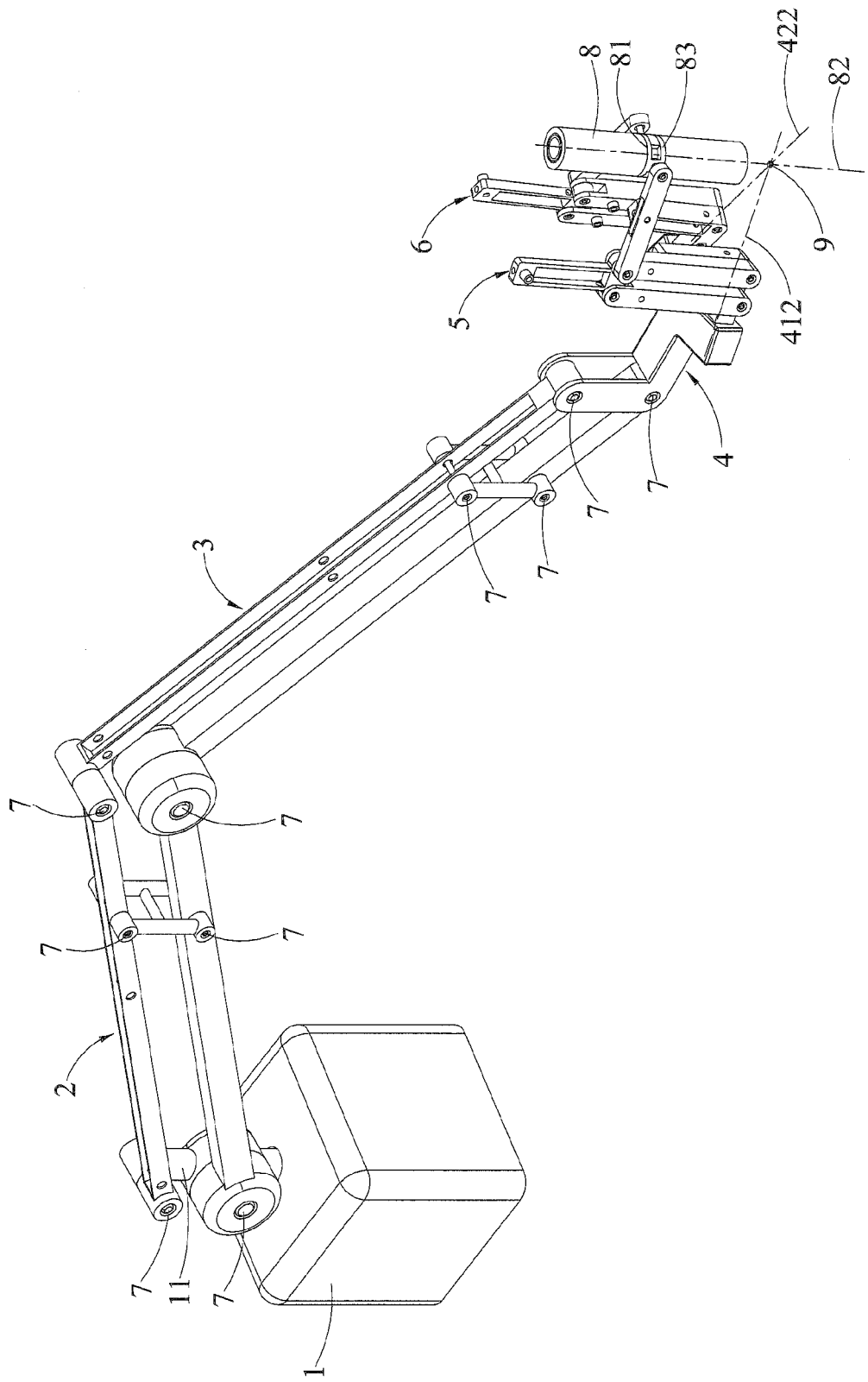
FIG. 1 is an overall schematic view of a surgical holder according to the present invention.

FIG. 1 is an overall schematic view of a surgical holder according to the present invention. The surgical holder includes a base unit 1, a first positioning unit 2, a second positioning unit 3, a connecting unit 4, a first orientating unit 5, and a second orientating unit 6. The base unit 1 comprises a primary link 11 and is adapted to stabilize the gravity of the surgical holder. The primary link 11 is disposed to be axially parallel to the direction of gravity horizontally disposed on the based unit 1. Please refer to FIG. 1 in conjunction with FIG. 2. The first positioning unit 2 comprises a first connecting link 21, a first auxiliary link 22 and at least a first pseudo base 23. The second positioning unit 3 comprises a second connecting link 31, a second auxiliary link 32 and at least a second pseudo base 33. One end of the first positioning unit 2 is pivotally connected to the primary link 11. One end of the first connecting link 21 and the first auxiliary link 22 pivotally connect to the primary link 11 respectively by means of a connecting component 7, thereby allowing the first connecting link 21 to move with respect to the connecting component 7 pivotally connected to the primary link 11 for position adjustment and so as the first auxiliary link 22. The first connecting link 21 and the first auxiliary link 22 have the same length. The first connecting link 21 and the first auxiliary link 22 are spaced apart within a distance to pivotally connect to the primary link 11, and the distance equals to the length of the first pseudo base 23. Two ends of the first pseudo base 23 are pivotally connected to the first connecting link 21 and the first auxiliary link 22 respectively via the connecting component 7. Because the spacing distance between the first connecting link 21 and the first auxiliary link 22 equals to the length of the first pseudo base 23, and also the first connecting link 21 and the first auxiliary link 22 have the same length, the position of the first pseudo base 23 pivotally connecting to the first connecting link 21 and the first auxiliary link 22 allow the primary link 11, the first connecting link 21, the first auxiliary link 22 and the first pseudo base 23 to substantially form four parallel connecting links. Therefore, all the connecting components 7 of the first positioning unit 2 are axially parallel to each other. In other words, the first connecting link 21 is parallel to the first auxiliary link 22, and the first pseudo base 23 is parallel to the primary link 11. When the first connecting link 21 and the first auxiliary link 22 move with respect to the primary link 11, the first pseudo base 23 will always be parallel to the primary link 11 regardless of its positions. In other words, the first pseudo base 23 would only be parallel to the gravity direction of the surgical holding device when it is operated.

One end of the second positioning unit 3 is pivotally connected to the other end of the first positioning unit 2. One end of the second connecting link 31 in the second positioning unit 3 is pivotally connected to one end in the first connecting link 21 that is not connected to the primary link 11 via the connecting component 7, and one end of the second auxiliary link 32 in the second positioning unit 3 is pivotally connected to one end in the first auxiliary link 22 that is not connected to the primary link 11. The second connecting link 31 and the second auxiliary link 32 have the same length, and the length of the second pseudo base 33 also equals to the first pseudo base 23. The two ends of the second pseudo base 33 are respectively connected to the second connecting link 31 and the second auxiliary link 32 operating effect therebetween. The second connecting link 31 is parallel to the second auxiliary link 32, the second pseudo base 33 is parallel to the primary link 11 and the first pseudo base 23, and all connecting components 7 in the second positioning unit 3 are axially parallel to each other, so as the connecting components 7 in the first positioning unit 2 that are axially parallel to each other. When the second connecting link 31 and the second auxiliary link 32 move with respect to the first positioning unit 2 or the base unit 1, the second pseudo base 33 will always be parallel to the primary link 11 and the first pseudo base 23 regardless of its positions. The second pseudo base 33 would only be parallel to the gravity direction of the surgical holding device when it is operated.

The number of the first pseudo base 23 and the second pseudo base 33 is at least one respectively. In an embodiment, two first pseudo base 23 and two second pseudo base 33 are used, a bar 25 is disposed between the two first pseudo bases 23 for connecting the two first grounding rods 23, and a bar 35 is disposed between the two second pseudo bases for connecting the two second pseudo bases 33. Note that the number of the first pseudo bases 23 and the second grounding rods 33 are not limited as described above.

The connecting unit 4 is pivotally connected to the other end of the second positioning unit 3. The third portions 43 of the connecting unit 4 are connected to the second connecting link 31 and the second auxiliary link 32 via two connecting components 7. In particular, the third portions 43 of the connecting unit 4 are connected to one end of the second connecting link 31 that is not connected to the first connecting link 21 via the connecting component 7, the third portions 43 of the connecting unit 4 are connected to one end of the second auxiliary link 32 that is not connected to the first auxiliary link 22 via the connecting component 7, and the distance between the two joints that connect to the second connecting link 31 and the second auxiliary link 32 respectively on the third portion 43 of the connecting unit 4 and the length of the second pseudo base 33 are equal. Further, all of the connecting components 7 in the connecting unit 4 are axially parallel to each other, so are the connecting components 7 in the first positioning unit 2 and the second positioning unit 3 axially parallel to each other. Therefore, the third portion 43 of the connecting unit 4, the second pseudo base 33, the second connecting link 31 and the second auxiliary link 32 also have the effects of four parallel connecting links. In other words, the third portion 43 of the connecting unit 4 would only be parallel to the gravity direction of the surgical holding device when it is operated.

Summarizing above, the plurality of connecting components 7 for use in the primary link 11, the first connecting link 21, the first auxiliary link 22, the first pseudo base 23, the second connecting link 31, the second auxiliary link 32, the second pseudo base 33 and the connecting unit 4 are all axially parallel to each other.

The end of the connecting unit 4 that is not pivotally connected to the second positioning unit 3 includes first and second portions 41, 42, and an included angle θ between the first and second portions 41, 42. The third portion 43 is perpendicular to the first and second portions 41, 42 but is not limited to this configuration. The first portion 41 has a first shaft hole 411 that has a first shaft direction 412. The second portion 42 has a second shaft hole 421 that has a second shaft direction 422. The first shaft direction 412 of the first shaft hole 411 and the second shaft direction 422 of the second shaft hole 421 intersect at one point, i.e., an intersection point 9. Therefore, the angle θ cannot be equal to 180 degrees and must be less than 180 degrees so that the first shaft direction 412 and the second shaft direction 422 can intersect at the intersection point 9.

Figure 3:
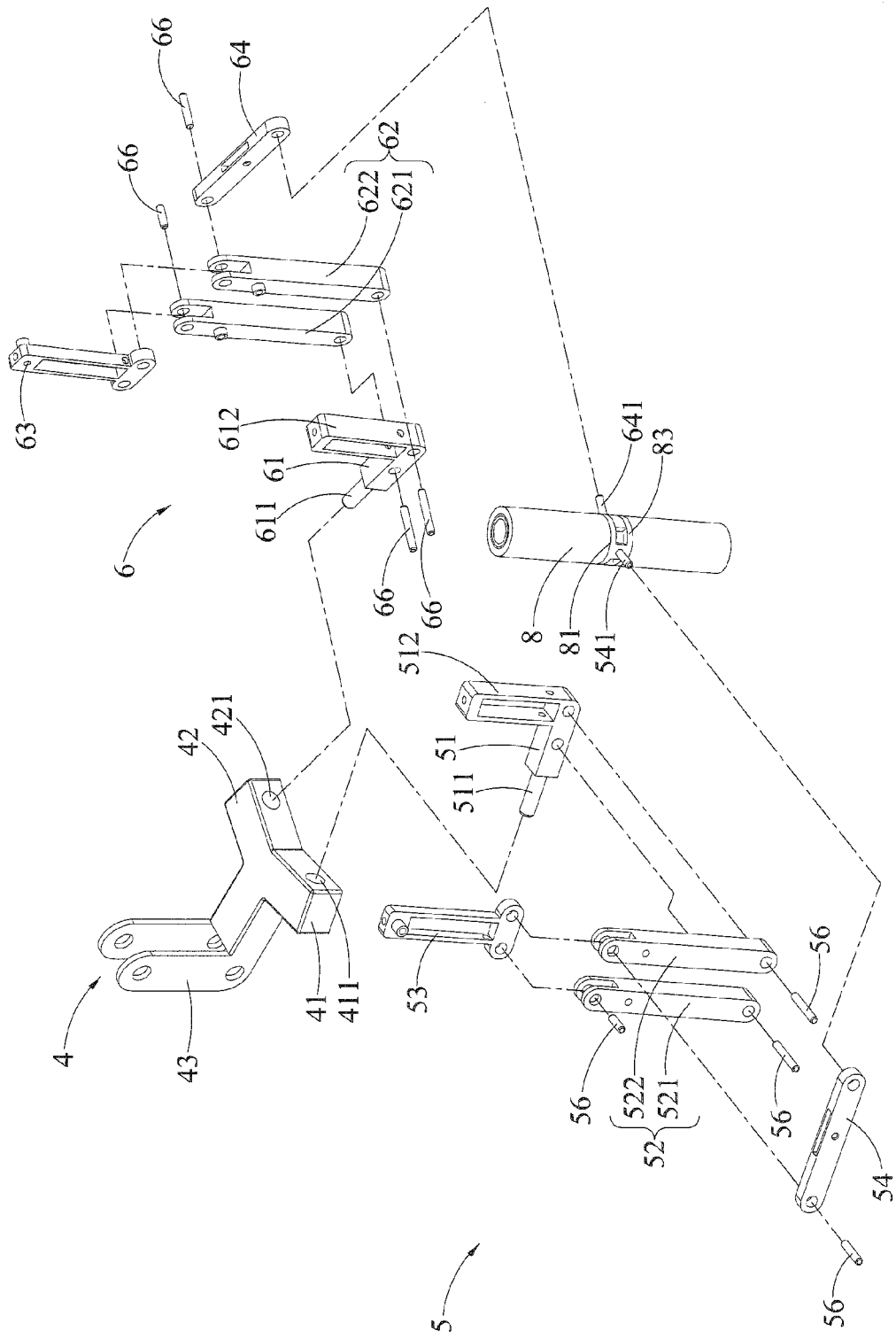
FIG. 3 is an exploded view of connecting unit, a first orientating unit, a second orientating unit and a sheath of the surgical holder according to the present invention.

Referring to FIGS. 1 and 3 at the same time, the first orientating unit 5 includes a first orientation link 51, a first parallel connecting link set 52, a third pseudo base 53 and a first supporting link 54. The second orientating unit 6 includes a second orientation link 61, a first parallel connecting link set 62, a fourth pseudo base 63 and a second supporting link 64. The first orientation link 51, the third pseudo base 53 and the first supporting link 54 collectively constitute the first orientating unit 5 via a plurality of first connecting members 56. The second orientation link 61, the fourth pseudo base 63 and the second supporting link 64 collectively constitute the second orientating unit 6 via a plurality of second connecting members 66. The first orientating unit 5 is substantially symmetrical to the second orientating unit 6.

The first orientation link 51 of the first orientating unit 5 includes a first shaft 511 and a first vertical portion 512 that is perpendicular to the first shaft 511 and the first orientation link 51. The first shaft 511 is adapted to pivotally connect to the first shaft hole 411 of the connecting unit 4. Therefore, the first orientation link 51 can rotate on the first shaft direction 412 with respect to the connecting unit 4. The second orientation link 61 of the second orientating unit 6 also has a second shaft 611 and a second vertical portion 612 that is perpendicular to the second shaft 611 and the second orientation link 61. The second shaft 611 is adapted to pivotally connect to the second shaft hole 421 of the connecting unit 4. Therefore, the second orientation link 61 can rotate on the second shaft direction 422 with respect to the connecting unit 4.

One end of the first parallel connecting link set 52 is pivotally connected to the first orientation link 51. One end of the third bar 521 and the third auxiliary link 522 in the first parallel connecting link set 52 is pivotally connected to the first orientation link 51 via two first connecting components 56 respectively, while the other end of the third bar 521 and the third auxiliary link 522 are pivotally connected to the third pseudo base 53 via two first connecting components 56. The plurality of first connecting components 56 used for the first parallel connecting link set 52 are axially parallel to each other. The length of the third bar 521 and the third auxiliary link 522 are equal, and the third bar 521 and the third auxiliary link 522 are disposed to be parallel to each other, thereby achieving four parallel bar operating effects between the third bar 521, the third auxiliary link 522, the first orientation link 51 and the third pseudo base 53. The third pseudo base 53 will be parallel to the first vertical portion 512 of the first orientation link 51 in the moving processing. The first supporting link 54 is pivotally connected to the third auxiliary link 522 and the third pseudo base 53 via a connecting component 56, and one end of the first supporting link 54 that is not pivotally connected to the third auxiliary link 522 has a first holding link 541. The first holding link 541 is connected on the first supporting link 54, and the shaft direction of the first holding link 541 is also parallel to the connecting components 56. The surface of the sheath 8 has a sliding groove 81 formed thereon and a ring body 83 corresponding to the sliding groove 81. The ring body 83 is able to slide within the sliding groove 81. The sliding groove 81 is perpendicular to the sheath shaft direction 82 in the surface extending direction of the sheath 8. The first holding link 541 abuts against the sliding groove 81 via the ring body 83 to slide with respect to the sliding groove 81.

One end of the second parallel connecting link set 62 is pivotally connected to the second orientation link 61. One end of the fourth bar 621 and the fourth auxiliary link 622 in the first parallel connecting link set 62 are pivotally connected to the second orientation link 61 via two second connecting components 66 respectively, while the other end of the fourth bar 621 and the fourth auxiliary link 622 are pivotally connected to the fourth pseudo base 63 via two second connecting components 66. The plurality of second connecting components 66 used for the second parallel connecting link set 62 are axially parallel to each other. The length of the fourth bar 621 and the fourth auxiliary link 622 are equal, and the fourth bar 621 and the fourth auxiliary link 622 are disposed to be parallel to each other, thereby achieving four parallel bar operating effects between the fourth bar 621, the fourth auxiliary link 622, the second orientation link 61 and the fourth pseudo base 63. The fourth pseudo base 63 will be parallel to the second vertical portion 612 of the second orientation link 61 in the moving processing. The second supporting link 64 is pivotally connected to the fourth auxiliary link 622 and the fourth pseudo base 63 via a second connecting component 66, and one end of the second supporting link 64 that is not pivotally connected to the fourth auxiliary link 622 has a second holding link 641. The second holding link 641 is connected on the second supporting link 64, and the shaft direction of the second holding link 641 is also parallel to the connecting components 66. The second holding link 641 also abuts against the sliding groove 81 of the sheath 8 to slide within the sliding groove. The sheath 8 has an endoscope installed therein, and because the ring body 83 slides within the sliding groove 81 of the sheath 8, the endoscope formed therein can rotate perceptively along the shaft direction 82 of the sheath 8. The ring body 83 is connected to the first holding link 541 and the second holding link 641 respectively, which are pivotally connected to the first supporting link 54 and the second supporting link 64 respectively, allowing the sheath 8 to move on the connecting unit 4 via the first orientating unit 5 and the second orientating unit 6. The sheath 8 can swing around right-and-left side on the connecting unit 4 via the first shaft hole 411 and the second shaft hole 421 to have a first yaw angle, and can also swing back and forth to have a second yaw angle. Irrespective of the angle (swing around or back and forth) of swinging of the sheath 8, the shaft direction 82 will always intersect at an intersection point 9 via the first shaft direction 412 of the first shaft 411 and the second shaft direction 422 of the second shaft 421. The intersection point 9 is a Remote center-of-motion, RCM point. Because the sliding groove 81 is perpendicular to the sheath shaft 82 in the surface extending direction of the sheath 8, when the sheath 8 rotates on the sheath shaft 82 via the sliding groove 81, the sheath shaft 82 will not deviate from the intersection point 9. The RCM point is a spatial fixed point along which the sheath 8 can spin around or shift to move flatly, which means that the endoscope installed in the sheath 8 will spin around along the RCM point. In laparoscopic surgery, if a surgical incision coincides with the RCM point, the installed endoscope can only rotate along the surgical incision and move forward in depth, which can prevent the expansion of wounds caused by incidental errors in lateral displacement of the operating surgeon.

Figure 2:
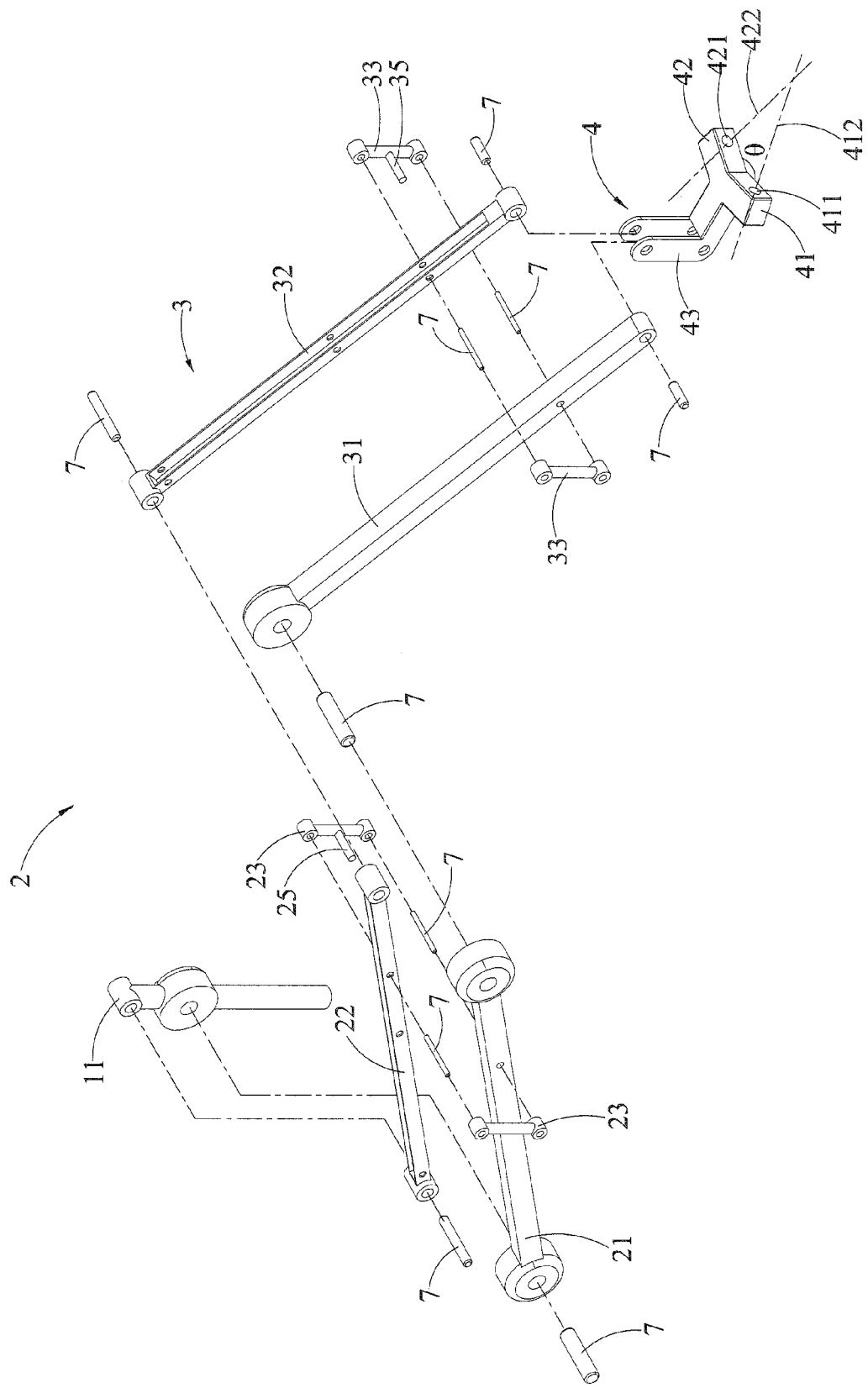
FIG. 2 is an exploded view of a base unit, a first positioning unit, a second positioning unit and a connecting unit of the surgical holder according to the present invention.
Figure 4:
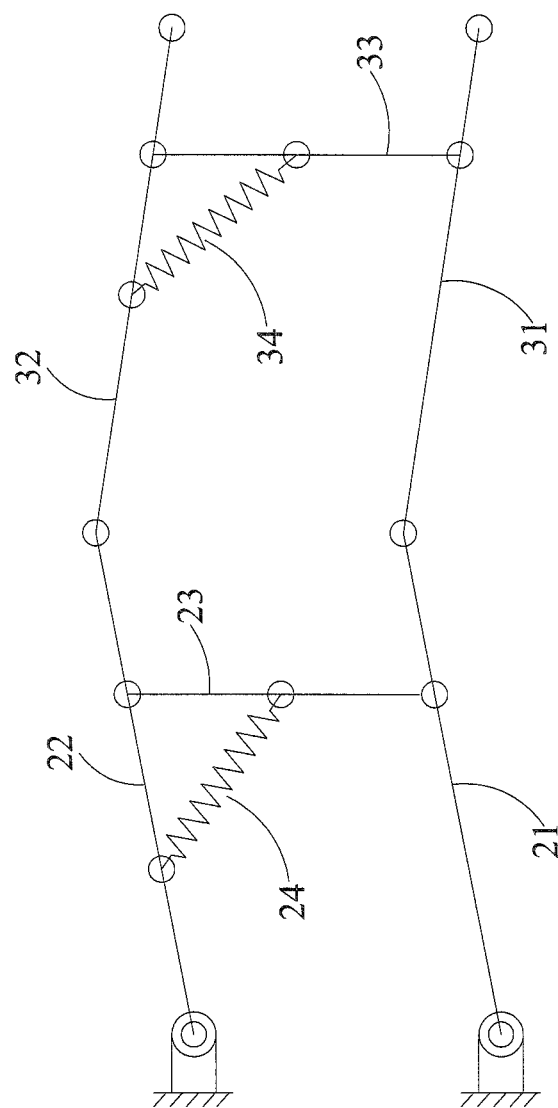
FIG. 4 is a schematic installation view of elastic elements built in the first positioning unit and the second positioning unit according to the present invention.

The first positioning unit 2 and the second positioning unit 3 are adapted to avoid the necessity of using any conventional mechanical latch connector or drive motor for locking/unlocking motions and thus achieving the static balance. Referring to FIGS. 2 and 4 at the same time, the first positioning unit 2 has a first elastic element 24 disposed therein, while the second positioning unit 3 has a second elastic element 34 disposed therein. Specifically, the first and second elastic elements 24, 34 are springs, which can either be stretch or twist springs and is not limited to the embodiment shown herein. The first elastic element 24 is disposed between the first pseudo base 23 and the first auxiliary link 22. Specifically, one end of the first elastic element is connected to a spot of the first auxiliary link 22, such as a mass center position, and the other end of the first elastic element 24 is connected to a spot of the first pseudo base 23, such as a mass center position thereof. The second elastic element 34 is disposed between the second pseudo base 33 and the second auxiliary link 32. Specifically, one end of the second elastic element 34 is connected to a spot of the second auxiliary link 32, such as a mass center position, and the other end of the second elastic element 34 is connected to a spot of the second pseudo base 33, such as a mass center position thereof. In an embodiment, the mass center of the first pseudo base 23 is at the position of the bar 25, and the mass center of the second pseudo base 33 is at the position of the bar 35. In addition, the first and second elastic elements 24, 34 may also use a spring with a rope as a simulated spring to become a zero free length spring but is not limited to this embodiment.

The elasticity of the first and second elastic elements 24, 34 can be obtained by means of static balance basic theory. When the surgical holder is required to maintain the state of static balance under arbitrary configurations, the elasticity of the springs is used to compensate for the changing variations of the gravity potential so that the overall potential of the mechanism is constantly maintained under any arbitrary configuration as shown in the following formula:

$$G_{all} + E = \text{constant}$$

Gall indicates the overall gravity potential of the mechanism, E indicates the elasticity potential of the spring. If the elasticity of the spring is Ks, and the quantity of one end of the spring connecting to the bar is m, the distance of the other end of the spring connecting to the bar is h, the length of the bar is b, and the distance of the bar mass center to other end of the bar is a, and the angle is θ, the elastic potential of the mechanism using x shaft as a standard gravity potential and the elastic potential of the spring are obtained respectively as follows:

$$G_{all} = -mga \cos \theta$$

$$E = \tfrac{1}{2} k s (h^2 + b^2 + 2hb \cos \theta)$$

To achieve the state of static balance in any condition, the overall potential of the above two formulas must be constant to obtain the following formula:

$$-mga \cos \theta + \tfrac{1}{2} k_s (b^2 + h^2) + k_s bh \cos \theta = \text{const}$$

Because only the angle θ will vary in the process of moving, and in order for the overall potential to remain a certain value, the total items relating to θ can be made as zero, that is:

$$-mga\cos\theta + k_s bh\cos\theta = 0$$

$$k_s = \frac{mga}{bh}$$

The elasticity of the spring can be obtained according to the above formula.

Therefore, the first positioning unit 2 and the second positioning unit 3 can use the first elastic element 24 and the second elastic element 34 to achieve the state of static balance in any arbitrary configuration. The first orientating unit 5 and the second orientating unit 6 can be assisted by the first elastic element 24 and the second elastic element 34 to enable the surgical holder to achieve the state of static balance in any arbitrary configuration.

Figure 5:
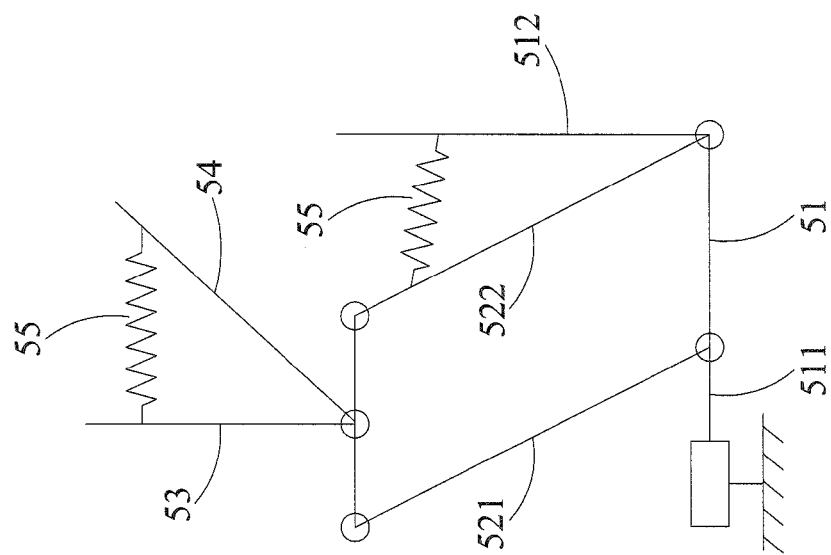
FIG. 5 is a schematic installation view of elastic elements built in the first orientating unit according to the present invention.

Referring to FIGS. 3 and 5 at the same time, FIG. 5 is an installation schematic view of the elastic element in the first orientating unit 5. The first orientating unit 5 has a plurality of third elastic elements 55 installed therein. In an embodiment, the number of the third elastic elements 55 is two, one of which is disposed on the first vertical portion 512 between the first parallel connecting link set 52 and the first orientation link 51, while the other of which is disposed at a position between the third pseudo base 53 and the first supporting link 54. Specifically, the two ends of one of the third elastic elements 55 are connected between the third auxiliary link 522 and the first vertical portion 512 respectively, and more specifically, the mass center position of the third auxiliary link 522 and the mass center position of the first vertical portion 512. In another embodiment, the two ends of one of the third elastic elements 55 may be connected between the third bar 521 and the first vertical portion 512 respectively, and more specifically, the mass center position of the third bar 521 and the mass center position of the first vertical portion 512 but is not limited to this disclosure. The two ends of another third elastic element 55 are respectively connected at a position between the third pseudo base 53 and the first supporting link 54. Specifically, the mass center position of the third pseudo base 53 and the mass center position of the first supporting link 54. However, the disposal of the third elastic element 55 is not limited to the mass center position as disclosed herein. The elasticity of the third elastic element can be obtained by means of the above static balance basic theory. In addition, the third elastic elements 55 may also use a spring with a rope as a simulated spring to become a zero free length spring but is not limited to this embodiment.

The first orientating unit 5 and the second orientating unit 6 are symmetrical, and the installation of the elastic elements in the second orientating unit 6 is the same as in the first orientating unit 5. The configuration of the elastic element in the second orientating unit 6 is briefly summarized as follows. The second orientating unit 6 has a plurality of fourth elastic elements 65 installed therein. In an embodiment, the number of the fourth elastic elements is two, one of which is disposed on the second vertical portion 612 between the second parallel connecting link set 62 and the second orientation link 61, while the other of which is disposed at a position between the fourth pseudo base 63 and the second supporting link 64. Specifically, the two ends of one of the third elastic elements 65 are connected between the fourth auxiliary link 622 and the second vertical portion 612 respectively, and more specifically, the mass center position of the fourth auxiliary link 622 and the mass center position of the second vertical portion 612. In another embodiment, the two ends of one of the fourth elastic elements 65 may be connected between the fourth bar 621 and the second vertical portion 612 respectively, and more specifically, the mass center position of the fourth bar 621 and the mass center position of the second vertical portion 612 but is not limited to this embodiment. The two ends of another fourth elastic element 65 are respectively connected at a position between the fourth pseudo base 63 and the second supporting link 64, specifically, the mass center position of the fourth pseudo base 63 and the mass center position of the second supporting link 64. However, the disposal of the fourth elastic element 65 is not limited to the mass center position as disclosed herein. The elasticity of the fourth elastic element can be obtained by means of the above static balance basic theory. In addition, the fourth elastic elements 65 may also use a spring with a rope as a simulated spring to become a zero free length spring but is not limited to this embodiment. Therefore, the first orientating unit 5 and the second orientating unit 6 can both achieve the state of static balance by using a plurality of third and fourth elastic elements 55, 65 respectively.

Summarizing above, the surgical holder according to the present invention can achieve the static balance by using a plurality of first, second third and fourth elastic elements. In addition, the first and second positioning units are adapted for positioning purposes, and the first and second orientating units are adapted for orientation purposes. The separate use of positioning and orientating units facilitates greater convenience and ease in operating the surgical holder. In the process of laparoscopic surgery, the first and second positioning units adapted for positioning purposes can be used first to move and position the endoscope installed in the surgical holder on the surgical incision of the patient to coincide the RCM point with the incision. Subsequently the first and second orientating units adapted for orientation purposes can then be used to limit and guide the endoscope so that it can only rotate along the surgical incision and move forward in depth, which can prevent the expansion of wounds caused by incidental errors in lateral displacement of the operating surgeon. Further, the use of elastic elements also allow the surgical holder to be maintained at the fixed position to facilitate operation without requiring conventional mechanic locking connector or any drive motor for locking/unlocking motions.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

What is claimed is:

1. A surgical holder, comprising:
   a base unit having a primary link;
   a first positioning unit having one end thereof pivotally connected to the primary link and having a first elastic element built therein;
   a second positioning unit having one end thereof pivotally connected to the other end of the first positioning unit and having a second elastic element built therein;
   a connecting unit having one end thereof pivotally connected to the other end of the second positioning unit and the other end including a first component having a first shaft hole and a second component having a second shaft hole, wherein an angle is included between the first component and the second component such that a shaft direction of the first shaft hole and a shaft direction of the second shaft hole intersect at a same point;
   a first orientating unit including a first orientation link, a first parallel connecting link set, a third pseudo base and a first supporting link, wherein the first orientation link has a first shaft rod pivotally connected to the first shaft hole, one end of the first parallel connecting link set is pivotally connected to the first orientation link, the other end of the first parallel connecting link set is pivotally connected to the third pseudo base and the first supporting link, and the first orientating unit has a plurality of third elastic elements built therein; and a second orientating unit including a second orientation link, a second parallel connecting link set, a fourth pseudo base and a second supporting link, wherein the second orientation link has a second shaft rod pivotally connected to the second shaft hole, one end of the second parallel connecting link set is pivotally connected to the second orientation link the other end of the second parallel connecting link set is pivotally connected to the fourth pseudo base and the second supporting link, and the second orientating unit has a plurality of fourth elastic elements built therein;

wherein the first elastic element, the second elastic element, the plurality of third elastic elements and the plurality of the fourth elastic elements balance the surgical holder statically.

2. The surgical holder as claimed in claim 1, wherein the first positioning unit further comprises a first connecting link, a first auxiliary link and at least a first pseudo base, one end of the first connecting link and one end of the first auxiliary link are pivotally connected to the primary link, two ends of the first pseudo base are pivotally connected to the first connecting link and the first auxiliary link, respectively, the first connecting link is parallel to the first auxiliary link, the first pseudo base is parallel to the primary link, and a shaft direction of the primary link is parallel to a gravity direction.

3. The surgical holder as claimed in claim 2, wherein two ends of the first elastic element are connected to a mass center position of the first pseudo base and a mass center position of the first auxiliary link, respectively.

4. The surgical holder as claimed in claim 3, wherein the second positioning unit further includes a second connecting link, a second auxiliary link and at least a second pseudo base, one end of the second connecting link is pivotally connected to the other end of the first connecting link, one end of the second auxiliary link is pivotally connected to the other end of the first connecting link, two ends of the second pseudo base are pivotally connected to the second connecting link and the second auxiliary link, respectively, the second connecting link is parallel to the second auxiliary link, and the second pseudo base is parallel to the primary link.

5. The surgical holder as claimed in claim 4, wherein two ends of the second elastic element are connected to a mass center position of the second pseudo base and a mass center position of the second auxiliary link, respectively.

6. The surgical holder as claimed in claim 4, further comprising a plurality of connectors for pivotally connecting with the primary link, the first connecting link, the first auxiliary link, the first pseudo base, the second connecting link, the second auxiliary link, the second pseudo base and the connecting unit, wherein the connectors are axially parallel to each other.

7. The surgical holder as claimed in claim 1, wherein the first parallel connecting link set includes a plurality of first pivot connectors each having its shaft direction parallel to each other, the second parallel connecting link set includes a plurality of second pivot connectors each having its shaft direction parallel to each other, a first holding link is disposed at one end of the first supporting link that is not pivotally connected to the first parallel connecting link set, a shaft direction of the first holding link is parallel to a shaft direction of the first pivot connectors, a second holding link is disposed at one end of the second supporting link that is not pivotally connected to the second horizontal connecting link, and a shaft direction of the second holding link is parallel to a shaft direction of the second pivot connectors.

8. The surgical holder as claimed in claim 7, further comprising a sheath having a sliding groove formed on a surface thereof, wherein the first holding link and the second holding link abut against the sliding groove to slide within the sliding groove, shaft directions of the sheath, the first shaft hole and the second shaft hole intersect at one point.

9. The surgical holder as claimed in claim 1, wherein the first elastic element, the second elastic element, the third elastic elements and the fourth elastic elements are springs.

10. The surgical holder as claimed in claim 1, wherein each of the third elastic elements is disposed between the first parallel connecting link set and a vertical portion of the first orientation link and between the third pseudo base and the first supporting link, each of the fourth elastic elements is disposed between the second parallel connecting link set and a vertical portion of the second orientation link and between the fourth pseudo base and the second supporting link, the third pseudo base is parallel to the vertical portion of the first orientation link, and the fourth pseudo base is parallel to the vertical portion of the second orientation link.

* * * * *